United States Patent
Härer et al.

(10) Patent No.: US 7,653,172 B2
(45) Date of Patent: Jan. 26, 2010

(54) METHOD FOR GENERATING TOMOGRAPHICAL RECORDINGS OF A PARTIALLY CYCLICALLY MOVING EXAMINATION OBJECT

(75) Inventors: Wolfgang Härer, Erlangen (DE); Holger Kunze, Bubenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 304 days.

(21) Appl. No.: 11/903,941

(22) Filed: Sep. 25, 2007

(65) Prior Publication Data
US 2008/0130826 A1    Jun. 5, 2008

(30) Foreign Application Priority Data
Sep. 27, 2006 (DE) .................... 10 2006 045 721

(51) Int. Cl.
*A61B 6/00* (2006.01)
(52) U.S. Cl. .............................. 378/8; 378/4
(58) Field of Classification Search .............. 378/4, 378/8
See application file for complete search history.

(56) References Cited

U.S. PATENT DOCUMENTS
2004/0136490 A1* 7/2004 Edic et al. ................ 378/4

OTHER PUBLICATIONS

Chiu et al., Tomographic Reconstruction of Time-Varying Object From Linear Time-Sequential sampled Projections, IEEE, 1994, pp. 309-312.*

De Man, B. u.a.: "An iterative algorithm for time-resolved reconstruction of a CT scan of a beating heart"; The 8$^{th}$ international meeting on fully three-dimensional image reconstruction in radiology and nuclear medicine, Jul. 2005, pp. 356-359.

Avinash C. Kak and Malcolm Slaney, "Principles of Computerized Tomographic Imaging", Kapitel 4.3, The Institute of Electrical and Electronics Engineers, New York, 1999, pp. i-x, 147-158.

Günter Lauritsch, Jan Boese, Lars Wigström, Herbert Kemeth and Rebecca Fahrig, "Towards Cardiac C-Arm Computed Tomography", IEEE Transactions on Medical Imaging, vol. 25, No. 7, Jul. 2006, pp. 922-934.

* cited by examiner

*Primary Examiner*—Edward J Glick
*Assistant Examiner*—Alexander H Taningco

(57) ABSTRACT

The invention relates to a method for generating tomographical recordings of a partially cyclically moving examination object by a tomography system and a tomography system, comprising the steps of: a spatial scanning of the examination object taking place using at least one detector, which generates detector output data; movement information of the moving subarea of the examination object being recorded during the scanning and being assigned to the detector output data or stored in a manner which correlates to the detector output data; and tomographical image data being reconstructed from the measured detector output data in a number of iteration steps. The invention is characterized in that iteration takes place in at least two iteration stages, with data records being used from the detector output data of different cycle phase regions in at least two iteration stages.

20 Claims, 3 Drawing Sheets

METHOD FOR GENERATING TOMOGRAPHICAL RECORDINGS OF A PARTIALLY CYCLICALLY MOVING EXAMINATION OBJECT

CROSS REFERENCE TO RELATED APPLICATIONS

This application claims priority of German application No. 10 2006 045 721.8 filed Sep. 27, 2006, which is incorporated by reference herein in its entirety.

FIELD OF THE INVENTION

The invention relates to a method for generating tomographical recordings of a partially cyclically moving examination object with the aid of a tomography system, with a spatial scanning of the examination object taking place using at least one detector, which generates detector output data, with movement information of the moving subarea of the examination object being recorded during scanning and assigned to the detector output data or being stored in a fashion which correlates with the detector output data, and tomographical image data being reconstructed from the measured detector output data in a number of iteration steps. Furthermore, the invention also relates to a tomography system which is designed to implement this method.

BACKGROUND OF THE INVENTION

Computer tomography (CT) provides a diagnosis and measuring method for medicine and testing technology, with the aid of which inner structures of a patient or test object can be examined, without having to carry out operative interventions on the patient or having to damage the testing object. A number of projections from different angles of view are recorded of the object to be examined. A 3D description of the object can be reconstructed from these projections.

A standard method used to solve this problem is presented by the generally known filtered back projection (FBP). This is an analytical method, with which the projections are filtered and back projected into the image region.

One problem for systems of this type is presented by examination objects, which move periodically at least in subareas. An example of this is the illustration of a patient in the area of a moving heart. Projections of a data record are not recorded from the same heart phase, e.g. the diastole, particularly for slow recording modalities, as is generally the case with C-arm systems. During one revolution, the heart can beat a number of times. This results in only one region of directly consecutively recorded projections being associated with the same heart phase. In connection with this region, a large angular gap results, which belongs to other heart phases and thus maps the heart in other movement situations, until projections result again which belong to the desired heart phase. Such projections, which were not recorded in a heart phase to be calculated, generally only differ however in subareas of the image, from those which were recorded during other heart phases. A reconstruction, without accounting for the fact that the individual projections do not belong to the same heart phase, generally results in distorted images of the object and in an increase in the number of artifacts also in object areas which were not moved.

A first, generally known approach (I) to solving this problem consists in omitting projections, which are not present in the desired heart phase and in reconstructing the remaining data record using a FBP reconstruction. The artifacts, which were generated as a result of the projections which were not suited to the heart phase, are herewith reduced, thereby causing artifacts to appear as a result of the missing projections.

A second, generally known approach (II) consists in consecutively recording a number of data records, and herewith ensuring that a complete set of projections is measured at each desired heart phase and that this overall data record is reconstructed by means of an FBP. This is complicated in terms of measurement technology and requires a highly stable heart rhythm.

The publication De Man, Edic, Basu: An iterative algorithm for time-resolved reconstruction of a CT scan of a beating heart. Proc. Eigth Int. Meeting on Fully Three-dimensional Image Reconstruction, SALT LAKE CITY, UTAH, Jul. 6-9, 2005, pp. 356-358, also discloses a third approach (III), in which the reconstruction from data of a revolution is proposed. An iterative reconstruction algorithm is used here, in which projections of all heart phases are used in each iteration cycle. In this way, during reconstruction, less account is taken of those projections which are not associated with the desired heart phase than of those from the desired heart phase. This method is problematical in that artifacts still appear in the reconstructed image data even with a higher iteration number.

SUMMARY OF THE INVENTION

The object of the invention is thus to provide an iterative reconstruction method, by means of which fewer artifacts appear in the final representation.

This object is achieved by the features of the independent claims. Advantageous developments of the invention are the subject matter of subordinate claims.

Inventors have identified that it is possible to implement an improved iterative reconstruction of cyclically moving objects, such as for instance the beating heart of a patient, by performing the iteration in a number of stages using differently selected data material in each instance. In this way, the selective restriction of the data material obtained over a number of movement cycles is to increase here with advancing iteration stages and is to finally contain the narrowest possible phase region of the movement cycle.

Iterative reconstruction methods are based on the principle that the measured projections Y are compared with the projections Y' calculated from the object which has already been approximately reconstructed and the error is subsequently used to correct the image of the object. In a typical formulation, the sought image in the nth iteration $X_n$ is calculated from the projection data Y with the aid of the update equation $$X_n = X_{n-1} + (R)(V)(Y - Y'_{n-1}), \text{ mit } Y'_{n-1} = (P)X_{n-1}$$

A suitable start image $X_0$, e.g. a zero image is at the start of the iteration. Here (P) represents the system matrix, with the aid of which the calculated projections Y' are determined from the scanned object image with knowledge of the scanning geometry, (R) represents the matrix of the back projection. (V) is a conditioning matrix, with which the convergence speed can be influenced. In the simplest case, it is a diagonal matrix with identical values, e.g. value 1.

As even projections which are not associated with the main observed movement and/or heart phase contain information relating to the sought image, it is proposed in accordance with the invention to firstly implement, in a first iteration stage, an iterative reconstruction with a minimal iteration number n, e.g. n=4, which takes account of all measured projections and to then use the reconstruction result thus obtained as a start image of a second iteration stage of an iterative reconstruction, which still only uses those projections for the reconstruction which were recorded in the observed movement and/or heart phase. This procedure is however not restricted to only two iteration stages, but can instead be extended to include a number of iteration stages.

In comparison with the method of the above-described approach (I) that rejects all projections which were recorded outside the heart phase, the method according to the invention is advantageous in that in the first part of the reconstruction, all projections are used for the reconstruction. The artifacts, which are produced as a result of the missing projections, can herewith be significantly reduced.

Compared with the above-illustrated approach (II), which reconstructs from a number of revolutions, the proposed method is advantageous in that this recording omits a number of data records, and/or can be restricted to considerably less data that is required for (II).

Compared with approach (III), the proposed method is advantageous in that fewer image artifacts are produced, since in the latter part of the reconstruction, only those projections are used for the reconstruction, which are consistent with the desired movement status of the object.

According to this knowledge, the inventor proposes improving a method for generating tomographical recordings of a partially cyclically moving examination object with the aid of a tomography system, with a spatial scanning of the examination object taking place using at least one detector, which generates detector output data, Movement information of the moving subarea of the examination object being recorded during the scanning and being assigned to the detector output data or stored in a manner which correlates with the detector output data and tomographical image data being reconstructed from the measured detector output data in a number of iteration steps.

Improving the invention herewith consists in iteration taking place in at least two iteration stages, with data records from the detector output data of different cycle phase regions being used in each instance in at least two iteration stages.

Reference is made here to the fact that data of a cycle phase region can originate in each instance from a number of or one individual movement cycle. The term "cycle phase region" thus describes, in a known manner, a specific time segment in the consecutive movement cycles of the partially cyclically moving examination object. This usually concerns the beating heart of a patient.

In accordance with the invention, the different cycle phase regions can overlap, with the cycle phase region of the second iteration stage possibly illustrating a subset of the cycle phase region of the first iteration stage.

The cycle phase region of a further second iteration stage can also illustrate a further subset of the cycle phase region of the first iteration stage. This means that a basis for further iteration stages is laid in the first short iteration stage, with a number of different phases of the moving subject and/or heart being able to be reconstructed with this same basis. For example the closure state of two heart valve can herewith be reconstructed in each instance to form a different heart phase in parallel with and by using the same basic reconstruction.

In a particularly favorable embodiment of the method according to the invention, the inventors also propose that:

an iterative reconstruction using a first reconstruction result be carried out from the detector output data in a first iteration stage without accounting for a cycle phase of the cyclically moving subarea of the examination object and a further iterative reconstruction be carried out in at least one second iteration stage exclusively with detector output data, which is to be assigned to a specific cycle phase of the cyclically moving subarea of the examination object, with the first reconstruction result being used as starting data.

With this method, detector data from the overall movement cycle can be used for reconstruction purposes in the first iteration stage, while in the at least one second iteration stage only detector data from an idle phase in the movement cycle, preferably an observed subarea of the examination object, is used for reconstruction purposes.

A specific maximum number of iteration cycles can be used for instance as a criterion for interrupting the iterations in at least one iteration stage.

The possibility also exists of using a specific difference in the reconstruction results of consecutive iteration cycles as a criterion for interrupting the iterations in at least one iteration stage.

Furthermore, a predetermined number n>1 of iteration cycles can be executed in the first iteration stage and a specific difference of the reconstruction results of consecutive iteration cycles can be used in the at least one second iteration stage.

The iteration can also be interrupted in the at least one second iteration stage, at the latest after a predetermined number m of iteration cycles has been reached.

The number n of iteration cycles in the first iteration stage can be set to be fewer than the maximum number m in the at least one second iteration stage after the achievement of which said iteration is interrupted.

In a particularly preferred variant of the method according to the invention, said method is applied to a patient with a beating heart. In this way, the movement information can be recorded by an ECG for instance and/or ECG information, e.g. the R wave in the ECG, is used for phase determination purposes. The use of other variants known in the prior art for detecting and recording movement information also lies within the scope of the invention, for instance measuring the heart function by taking a mechanical pressure pulse, recording a kymogram for detecting heart and/or lung movements or using lung function measurements in order to detect lung movements. The lung per se can also be observed as a moving subarea.

The proposed method can be used in conjunction with a tomography system, which obtains image data from projective mappings by means of ionizing radiation, an x-ray CT system for instance or x-ray C-arm system, in which at least one radiation source is moved in a circular or helical fashion about the examination object, in particular the patient. In conjunction with the x-ray CT system, reference is made in detail to the fact that the described method can be used both with CT systems having an individual focus detector system as well as with two or more focus detector systems which are arranged angularly offset from one another. With the latter embodiment, projection data, which is simultaneously used for iterative reconstruction, also originates from different focus detector systems, with a higher time resolution of the system being achieved in a known fashion.

Alternatively, the above-described method can also be used in conjunction with a magnetic resonance tomography system or an ultrasound tomography system.

The inventors also further propose a tomography system having a control and computing unit, containing a data storage device for storing programs and at least one processor for executing stored programs, with at least one of the stored programs executing the afore-mentioned method.

BRIEF DESCRIPTION OF THE DRAWINGS

The invention is described in more detail below with reference to a preferred exemplary embodiment with the aid of the figures, with only the features needed to understand the invention being displayed, the subsequent reference characters are used here: 1: tomography system; 2: first x-ray tube; 3: first detector; 4: second x-ray tube; 5: second detector; 6: gantry housing; 7: patient; 8: patient couch; 9: system axis; 10: control and computing unit; 11: data storage device; 12: C-arm; 21.a: measured projections of all heart phases; 21.b: measured projections of the desired heart phase; 22: starting image; 23: reconstructed image according to the n'th iteration; 24: determination of the calculated projections; 25: calculated projections; 26: difference determination between calculated projections and measured projections (error calculation); 27: back projection of the error; 28: totals formation from back projection of the error and of the reconstructed image; 29: changeover switch, which, after a predetermined number of iteration cycles, switches from projections 21.a (all heart phases) to projections 21.b (only desired heart phase); $Prg_n$: computer program, in which.

DETAILED DESCRIPTION OF THE INVENTION

Figure 1:
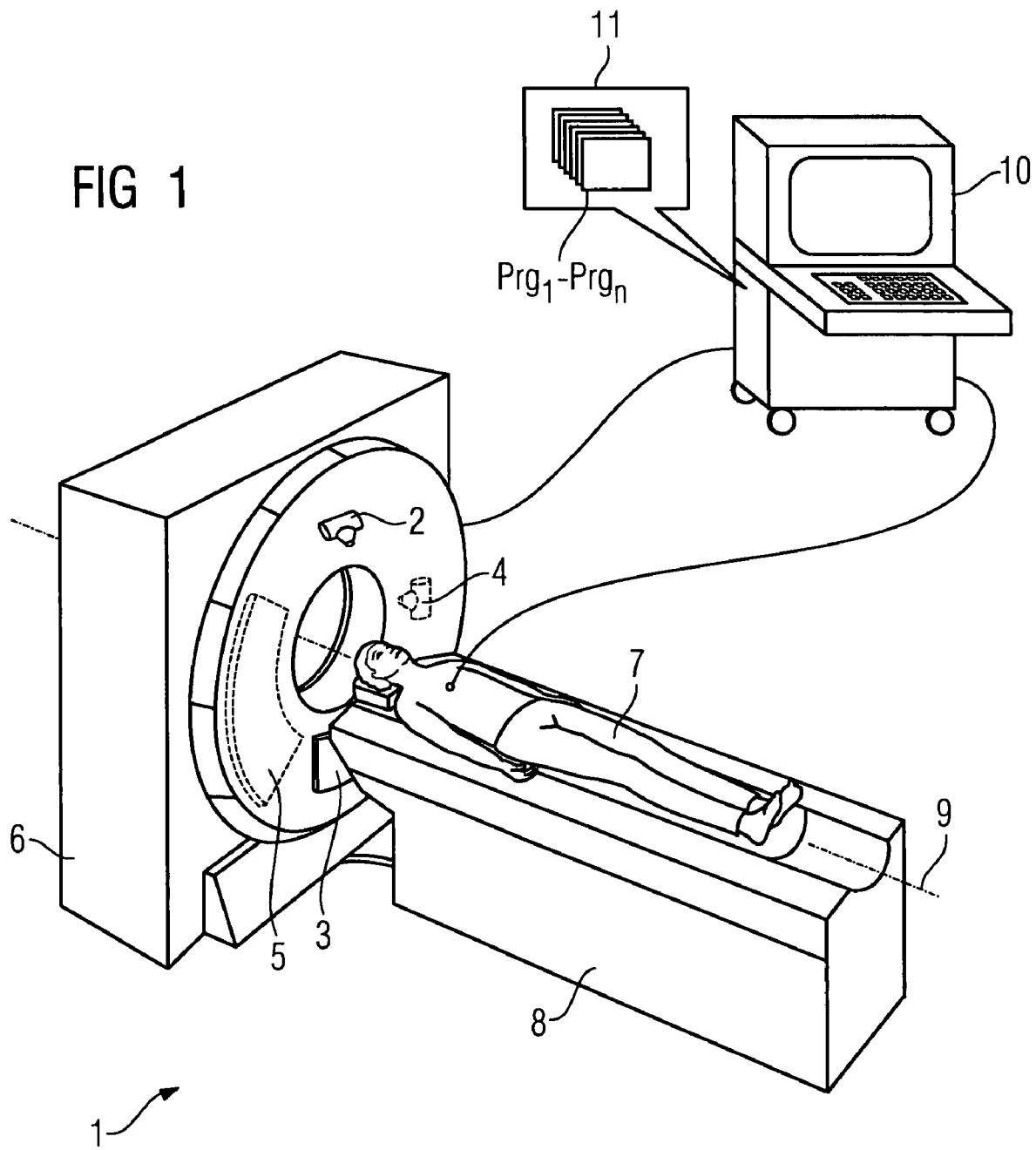
FIG. 1: shows a detailed view of an x-ray CT system for implementing the method according to the invention.

FIG. 1 shows an exemplary x-ray CT system 1, upon which the afore-described method can be implemented. The x-ray CT system 1 has a gantry housing 6 with a first x-ray tube 2 and detector 3 which is arranged opposite thereto, which are disposed on a gantry (not shown in further detail here) within the gantry housing 6. The control and data evaluation take place by means of the control and computing unit 10 using the programs $Prg_1$-$Prg_n$ contained in the data storage device 11. For the scan, the patient 7 illustrated on the moveable patient couch 8 is moved into the measurement range between the x-ray tube 2 and detector 3 along the system axis 9, so that during a rotation of the gantry, the patient 7 can be scanned. An ECG is simultaneously taken of the patient by way of an additional line, so that the corresponding movement information can be extracted in order to implement the method according to the invention. In addition to the first x-ray tube 2 and the first detector 3, a second x-ray tube 4 and a second detector 5 can optionally also be arranged on the gantry, thereby achieving a higher scanning rate. The method according to the invention is stored in programs $Prg_1$-$Prg_n$ and can be recalled and executed by the computing unit if necessary.

Figure 2:
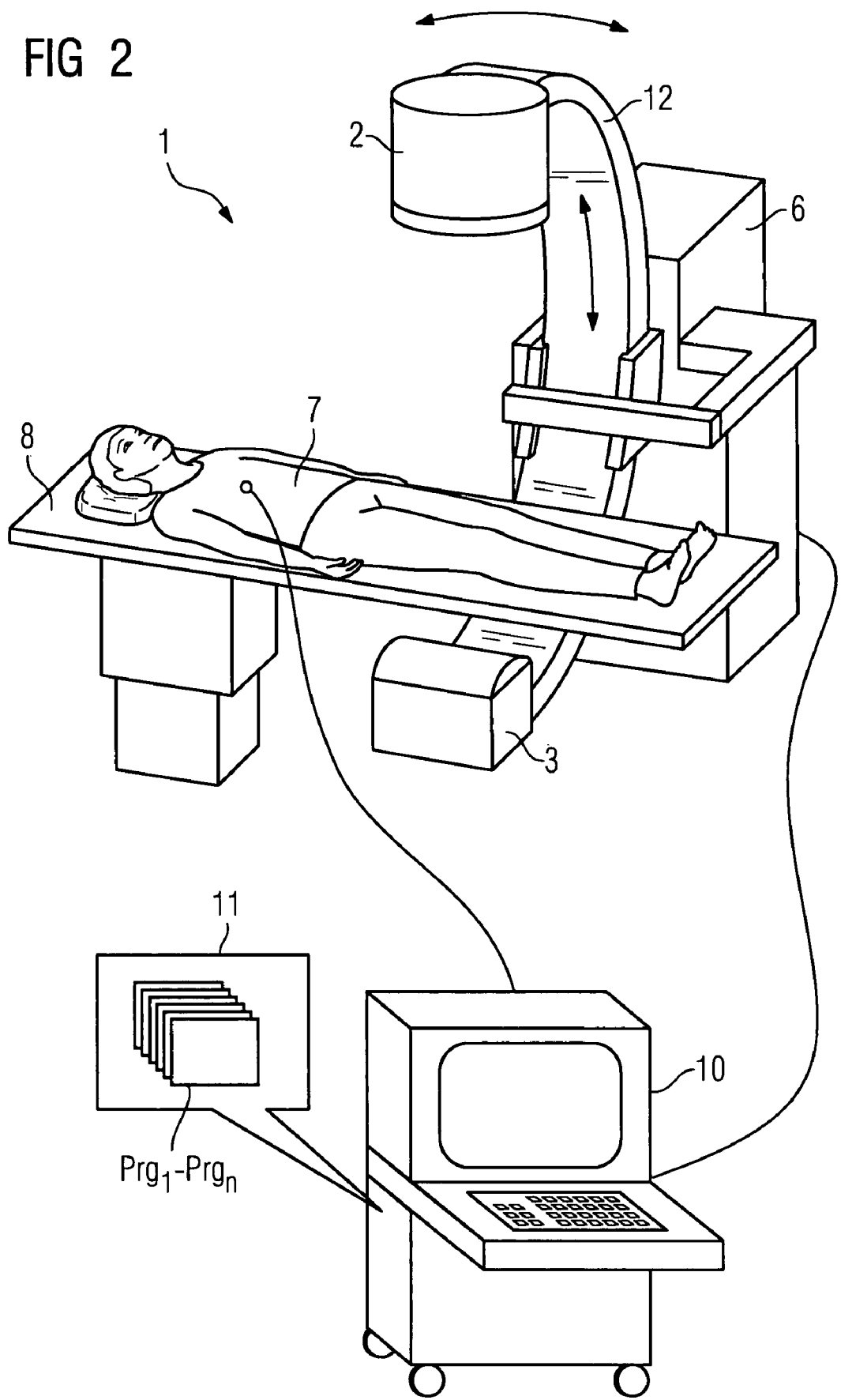
FIG. 2: shows a detailed view of an x-ray C-arm system for implementing the method according to the invention.

FIG. 2 illustrates an embodiment of a CT system which is preferred for the method, namely a C-arm system 1, which comprises a C-arm 12 on the housing 6, said C-arm 12 being rotatable about a patient 7, with an x-ray tube 2 being arranged on one end of the C-arm and a detector 3 being arranged on the other end of the C-arm. The patient 7 is located on a moveable patient couch 8, thereby allowing said patient 7 with the subarea to be observed to be moved in each instance into the measurement field between x-ray tube 2 and detector 3 of the C-arm system. A control and computing unit 10 having a data storage device 11 assumes control of the system in this case, by allowing corresponding control and reconstruction programs $Prg_1$-$Prg_n$ to run if necessary.

Figure 3:
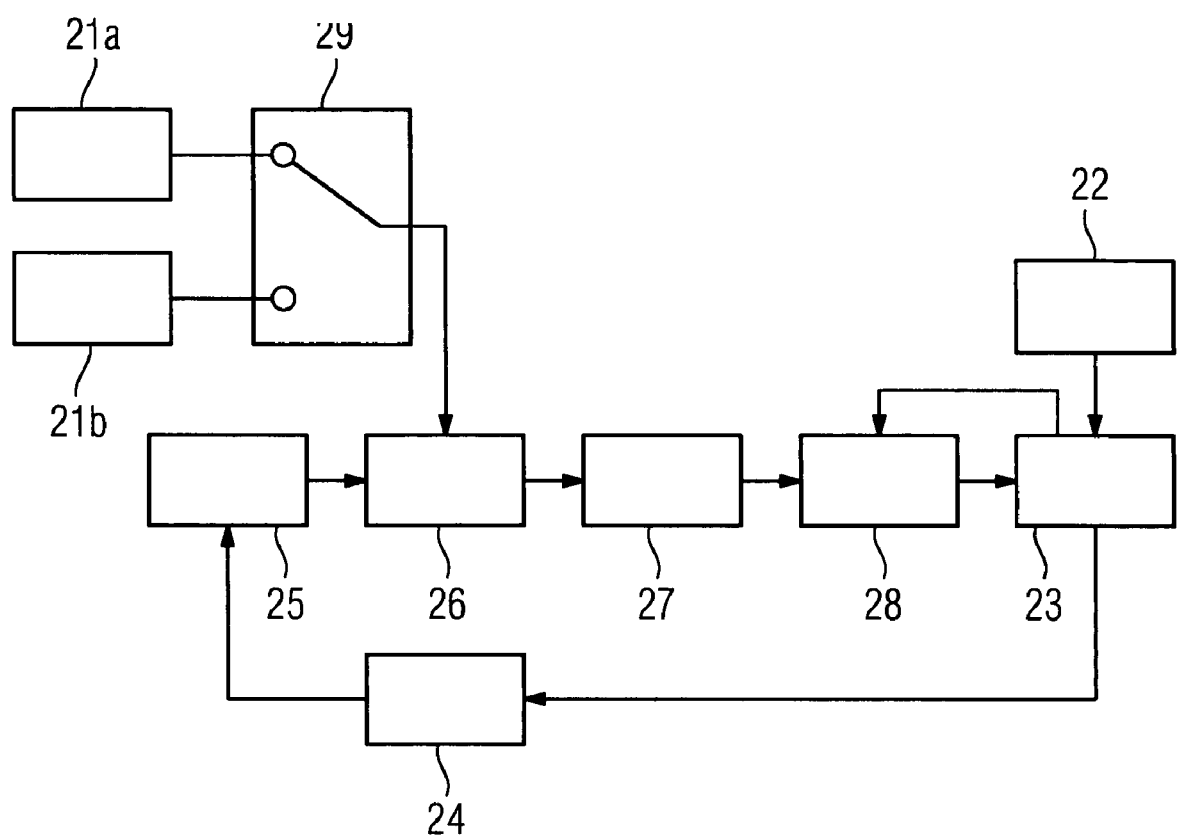
FIG. 3: shows a detailed view of a schematic illustration of a preferred variant of a two-stage iteration method.

A preferred embodiment of the method according to the invention is shown schematically in FIG. 3.

The measured projections of all heart phases 21a are firstly fed to an iterative image reconstruction 22-28, followed then by the measured projections of the desired heart phase 21b. The selection is carried out by a changeover switch 29, which, after a specific number of iteration steps, switches from 21a to 21b.

Iteration proceeds as follows: A starting image 22 is adopted in the data storage device of the reconstructed image 23. This starting image can consist of any pre-allocation, also with zeros or of an approximation image of the object to be mapped. Projections 25 calculated in step 24 are determined from this image 23. The difference ("error") 26 between the calculated projections 25 and the projections measured and selected in each instance by the changeover switch is then determined. Projections of all heart phases 21a are then used at the start. These difference projections are then back-projected 27 into the image volume and added 28 to the image 23. An iteration cycle thus runs and the image 23 contains a first reconstruction result, the quality of which can be successively improved by repeating the described steps. After a specific number of iteration steps, moving the changeover switch no longer means that projections of all heart phases 21a are fed to the method but instead only the projections 21b of the desired heart phase.

It is understandable that the afore-mentioned features of the invention can not only be used in the combination specified in each instance, but can however also be used in other combinations or in isolation, without abandoning the scope of the invention.

The invention claimed is:

1. A method for generating a tomographical image data of a cyclically moving examination object by a tomography system, comprising:
   generating a detector output data by spatially scanning the examination object with a detector of the tomography system;
   recording a movement information of the moving examination object during the scanning;
   assigning the movement information to the detector output data; and
   reconstructing the tomographical image data by iterating data records from the detector output data of different cycle phase regions in at least two iteration stages.

2. The method as claimed in preceding claim 1, wherein the different cycle phase regions are overlapped.

3. The method as claimed in preceding claim 2, wherein a cycle phase region of the second iteration stage is a subset of a cycle phase region of the first iteration stage.

4. The method as claimed in preceding claim 3, wherein a cycle phase region of a further second iteration stage is a further subset of a cycle phase region of the first iteration stage.

5. The method as claimed in preceding claim 1,
   wherein a first reconstruction result is iterated in the first iteration stage from the detector output data taking account of all different cycle phases of the moving examination object, and
   a further reconstruction result is iterated in the second iteration stage from the detector output data assigned to a specific cycle phase region of the moving examination object with the first reconstruction result as a starting data.

6. The method as claimed in preceding claim 1, wherein a detector output data from an overall movement cycle is used in the first iteration stage for reconstruction.

7. The method as claimed in preceding claim 1, wherein a detector output data from an idle phase in a movement cycle is used exclusively in the second iteration stage for reconstruction.

8. The method as claimed in preceding claim 1, wherein a specific maximum number of iteration steps is used as a criterion for interrupting the iteration in at least one of the iteration stages.

9. The method as claimed in preceding claim 1, wherein a specific difference in reconstruction results of consecutive iteration steps is used as a criterion for interrupting the iteration in at least one of the iteration stages.

10. The method as claimed in preceding claim 1,
wherein a predetermined number of iteration steps is used as a criterion for interrupting the iteration in the first iteration stage, and
wherein a specific difference in reconstruction results of consecutive iteration steps is used as a criterion for interrupting the iteration in the second iteration stage.

11. The method as claimed in preceding claim 1, wherein the iteration is interrupted in the second iteration stage at the latest after a predetermined number of iteration steps has been reached.

12. The method as claimed in preceding claim 1, wherein iteration steps in the first iteration stage is fewer than iteration steps in the second iteration stage.

13. The method as claimed in preceding claim 1, wherein the moving examination object is a beating heart of a patient.

14. The method as claimed in preceding claim 13, wherein the movement information is an ECG of the beating heart of the patient.

15. The method as claimed in preceding claim 1, wherein the tomography system is selected from the group consisting of: an x-ray CT system, an x-ray C-arm system, a magnetic resonance tomography system, and an ultrasound tomography system.

16. The tomography system for generating a tomographical image data of a cyclically moving examination object, comprising:
a detector that generates a detector output data by spatially scanning the examination object;
a device that records a movement information of the moving examination object during the scanning; and
a computing device that reconstructs the tomographical image data by iterating data records from the detector output data of different cycle phase regions in at least two iteration stages.

17. The tomography system as claimed in claim 16, wherein the different cycle phase regions are overlapped.

18. The tomography system as claimed in claim 16,
wherein a first reconstruction result is iterated in the first iteration stage from the detector output data taking account of all different cycle phases of the moving examination object, and
a further reconstruction result is iterated in the second iteration stage from the detector output data assigned to a specific cycle phase region of the moving examination object with the first reconstruction result as a starting data.

19. The tomography system as claimed in claim 16, wherein a specific maximum number of iteration steps is used as a criterion for interrupting the iteration in at least one of the iteration stages.

20. The tomography system as claimed in claim 16, wherein a specific difference in reconstruction results of consecutive iteration steps is used as a criterion for interrupting the iteration in at least one of the iteration stages.

* * * * *